(12) United States Patent
Castinado et al.

(10) Patent No.: US 11,152,086 B2
(45) Date of Patent: Oct. 19, 2021

(54) ELECTROENCEPHALOGRAM TRIGGERED EXPERIENCE MODIFICATION SYSTEM

(71) Applicant: BANK OF AMERICA CORPORATION, Charlotte, NC (US)

(72) Inventors: Joseph Benjamin Castinado, North Glenn, CO (US); Charles Russell Kendall, Snoqualmie, WA (US)

(73) Assignee: BANK OF AMERICA CORPORATION, Charlotte, NC (US)

( * ) Notice: Subject to any disclaimer, the term of this patent is extended or adjusted under 35 U.S.C. 154(b) by 405 days.

(21) Appl. No.: 15/802,036

(22) Filed: Nov. 2, 2017

(65) Prior Publication Data
US 2019/0131002 A1 May 2, 2019

(51) Int. Cl.
| | |
|---|---|
| *G16H 10/60* | (2018.01) |
| *G16H 80/00* | (2018.01) |
| *G16H 40/63* | (2018.01) |
| *A61B 5/00* | (2006.01) |
| *A61B 5/369* | (2021.01) |
| *A61B 5/316* | (2021.01) |

(52) U.S. Cl.
CPC ........... *G16H 10/60* (2018.01); *A61B 5/0006* (2013.01); *A61B 5/369* (2021.01); *G16H 40/63* (2018.01); *G16H 80/00* (2018.01); *A61B 5/316* (2021.01)

(58) Field of Classification Search
None
See application file for complete search history.

(56) References Cited

U.S. PATENT DOCUMENTS

| | | | |
|---|---|---|---|
| 3,848,586 | A | 11/1974 | Suzuki et al. |
| 5,495,853 | A | 3/1996 | Yasushi |
| 5,626,145 | A | 5/1997 | Clapp et al. |
| 5,687,291 | A | 11/1997 | Smyth |
| 6,021,346 | A | 2/2000 | Ryu et al. |
| 6,092,058 | A | 7/2000 | Smyth |
| 6,317,627 | B1 | 11/2001 | Ennen et al. |
| 6,488,617 | B1 | 12/2002 | Katz |
| 6,496,724 | B1 | 12/2002 | Levendowski et al. |
| 6,735,467 | B2 | 5/2004 | Wilson |
| 7,035,685 | B2 | 4/2006 | Ryu et al. |

(Continued)

OTHER PUBLICATIONS

"Profile." Merriam-Webster.com. 2020. www.merriam-webster.com (May 29, 2020). (Year: 2020).*

(Continued)

*Primary Examiner* — Matthew Kremer
*Assistant Examiner* — Samuel C Kim
(74) *Attorney, Agent, or Firm* — Michael A. Springs; Moore & Van Allen PLLC; Nicholas C. Russell

(57) ABSTRACT

Embodiments of the invention are directed to systems, methods, and computer program products for collection of and utilization of electroencephalography (EEG) data for user experience and interaction management. The invention interconnects with a network for real-time user experience modification based on user identification via EEG data. In this way, upon recognition and analysis of EEG data, the invention forms and modify a user specific experience via integration within third party systems. EEG readings are segmented, sorted, and matched to a user baseline EEG reading to identify the user and modify the user experience based on quantifiable points.

20 Claims, 5 Drawing Sheets

(56) References Cited

U.S. PATENT DOCUMENTS

| | | |
|---|---|---|
| 7,299,088 B1 | 11/2007 | Thakor et al. |
| 8,135,957 B2 | 3/2012 | Dinges et al. |
| 8,457,595 B2 | 6/2013 | MacInnis et al. |
| 9,058,473 B2 * | 6/2015 | Navratil ................. G06F 21/32 |
| 9,268,876 B2 | 2/2016 | MacInnis et al. |
| 9,473,493 B2 | 10/2016 | Jayaraman et al. |
| 9,489,596 B1 * | 11/2016 | Khosla ................. G06K 9/6263 |
| 10,154,818 B2 | 12/2018 | Zhang et al. |
| 10,176,894 B2 | 1/2019 | Park et al. |
| 10,482,227 B2 * | 11/2019 | Chen ..................... A61B 5/117 |
| 2004/0077966 A1 | 4/2004 | Yamaguchi et al. |
| 2004/0077967 A1 | 4/2004 | Jordan |
| 2005/0085872 A1 | 4/2005 | Yanagihara et al. |
| 2006/0135879 A1 | 6/2006 | Liley |
| 2007/0198432 A1 * | 8/2007 | Pitroda ................. G06F 21/606 705/64 |
| 2010/0191140 A1 | 7/2010 | Terada et al. |
| 2010/0317988 A1 | 12/2010 | Terada et al. |
| 2011/0071416 A1 | 3/2011 | Terada et al. |
| 2012/0108995 A1 | 5/2012 | Pradeep et al. |
| 2014/0159862 A1 | 6/2014 | Yang et al. |
| 2014/0178843 A1 | 6/2014 | Smyth |
| 2014/0223462 A1 * | 8/2014 | Aimone ................. A61B 5/369 725/10 |
| 2015/0081226 A1 | 3/2015 | Baki |
| 2015/0294085 A1 | 10/2015 | Kare et al. |
| 2016/0004862 A1 | 1/2016 | Almehmadi et al. |
| 2016/0183812 A1 | 6/2016 | Zhang et al. |
| 2016/0188839 A1 | 6/2016 | Kaul et al. |
| 2017/0118204 A1 | 4/2017 | Laine et al. |
| 2017/0196501 A1 | 7/2017 | Watson et al. |
| 2017/0228512 A1 | 8/2017 | Driscoll |
| 2017/0323073 A1 | 11/2017 | Westermann et al. |

OTHER PUBLICATIONS

"Configuration." Merriam-Webster.com. 2020. www.merriam-webster.com (May 29, 2020). (Year: 2020).*

Ruiz-Blondet et al., CEREBRE: A Novel Method for Very High Accuracy Event-Related Potential Biometric Identification, IEEE Transactions on Information Forensics and Security, Jul. 2016, vol. 11, No. 7, pp. 1618-1629.

Ruiz-Blondet et al., Permance of the CEREBRE brain biometric protocol, Pattern Recognition Letters, 2017, vol. 95, pp. 37-43.

* cited by examiner

ELECTROENCEPHALOGRAM TRIGGERED EXPERIENCE MODIFICATION SYSTEM

BACKGROUND

With advancements in technology, use of electroencephalography (EEG) and access to EEG devices are becoming more prevalent.

BRIEF SUMMARY

The following presents a simplified summary of one or more embodiments of the invention in order to provide a basic understanding of such embodiments. This summary is not an extensive overview of all contemplated embodiments, and is intended to neither identify key or critical elements of all embodiments, nor delineate the scope of any or all embodiments. Its sole purpose is to present some concepts of one or more embodiments in a simplified form as a prelude to the more detailed description that is presented later.

Electroencephalography (EEG) is a monitoring method to record electrical activity of the brain, and is a non-invasive approaches to brain computer interfacing, mainly due to its fine temporal resolution, ease of use, and portability. EEG devices are portable, such as a wearable device that may utilize a low power wireless connection and dry electrodes.

In some embodiments, the invention utilizes EEG resources to manage device user experiences. In this way, the invention interconnects with a network for real-time data transfer from user devices, third party systems, and other connected devices to receive, analyze, and react to EEG data from an EEG reader. As such, upon receiving and analyzing specific user based EEG data, the system may form and activate a user specific EEG configuration and react by sending control signals to user devices for management of the user's experience.

Embodiments of the invention relate to systems, methods, and computer program products for: identifying, via an EEG reader, a baseline EEG reading corresponding to a user, generating a user specific EEG configuration for the user based on spectral analysis of a set of predetermined attributes of the baseline EEG reading, storing the user specific EEG configuration in a user configuration repository, wherein the user specific EEG configuration further comprises user preferences for experience modifications, receiving a trigger signal associated with a user activity initiated by the user, in response to the trigger signal, transmitting a control signal to cause the EEG reader to capture a subsequent EEG reading, receiving, from the EEG reader, the subsequent EEG reading, confirming that the subsequent EEG reading corresponds to the user specific EEG configuration for the user by using comparative spectral analysis of the subsequent EEG reading and the baseline EEG reading and identifying that predetermined attributes of the subsequent EEG reading match the predetermined attributes of the baseline EEG reading associated with the user, and transmitting a control signal to a device in proximity to the user activity, wherein the control signal is configured to customize a component of the device in accordance with the user specific EEG configuration, and wherein customizing the component of the device causes a change in the user's experience.

In some embodiments, the control signal transmitted to the device in proximity to the user activity is configured to customize the component of the device in response to the subsequent EEG reading by applying a previously stored user preference associated with the user activity and user device.

In some embodiments, the system is further configured to receive, from the EEG reader, the subsequent EEG reading and transmit, to a third party system, a control signal, wherein the control signal is configured to customize a component of the third party system and wherein customizing the component of the third party system changes the user's experience at the third party system.

In some embodiments, the user specific EEG configuration for the user further comprises analyzing frequency content for the baseline EEG reading time-locked to a known event or stimulus, detecting periodicities, patterns, and component frequencies present in the baseline EEG reading, and storing the periodicities, patterns, and component frequencies for the baseline EEG reading in the user specific EEG configuration.

In some embodiments, performing the comparative spectral analysis of the subsequent EEG reading and the baseline EEG reading further includes comparing predetermined attributes of the baseline EEG reading and the subsequent EEG reading to identify a match or partial match for the user, and generating a confidence that the subsequent EEG reading is an EEG reading of the user based on a comparative analysis to the baseline EEG reading for the user.

In some embodiments, identifying the baseline EEG reading further comprises recording an EEG signal for the user at a time interval of at least 300 milliseconds after a known event or stimulus.

In some embodiments, the system is further configured to interface with multiple users at one time and transmit a series of control signals to customize discrete components of the user device, a set of user devices, or a smart system in response to subsequent EEG readings for the multiple users, and wherein customizing the discrete components causes a change in the experience of each of the multiple users.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Figure 1:
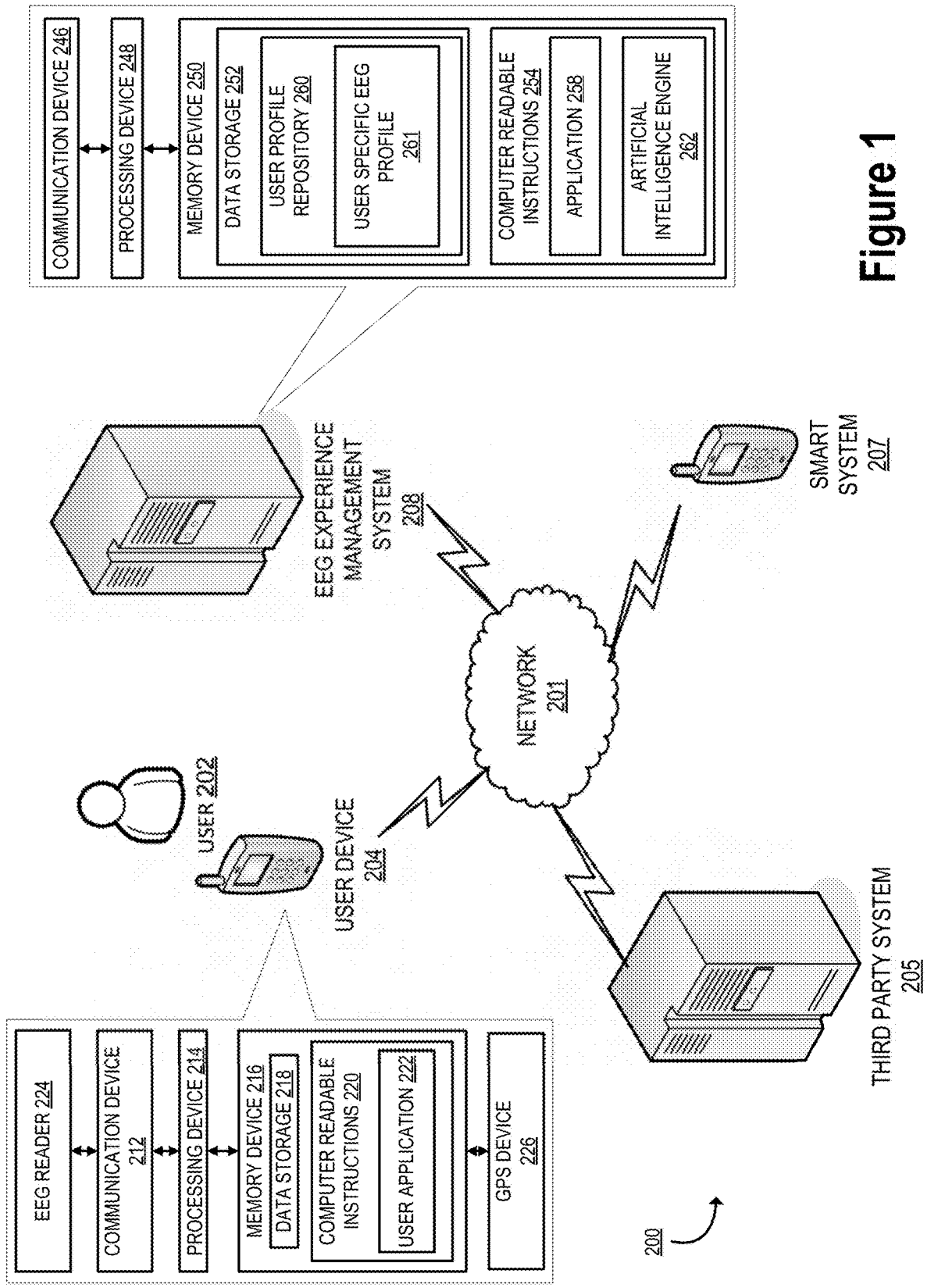
Figure 2:
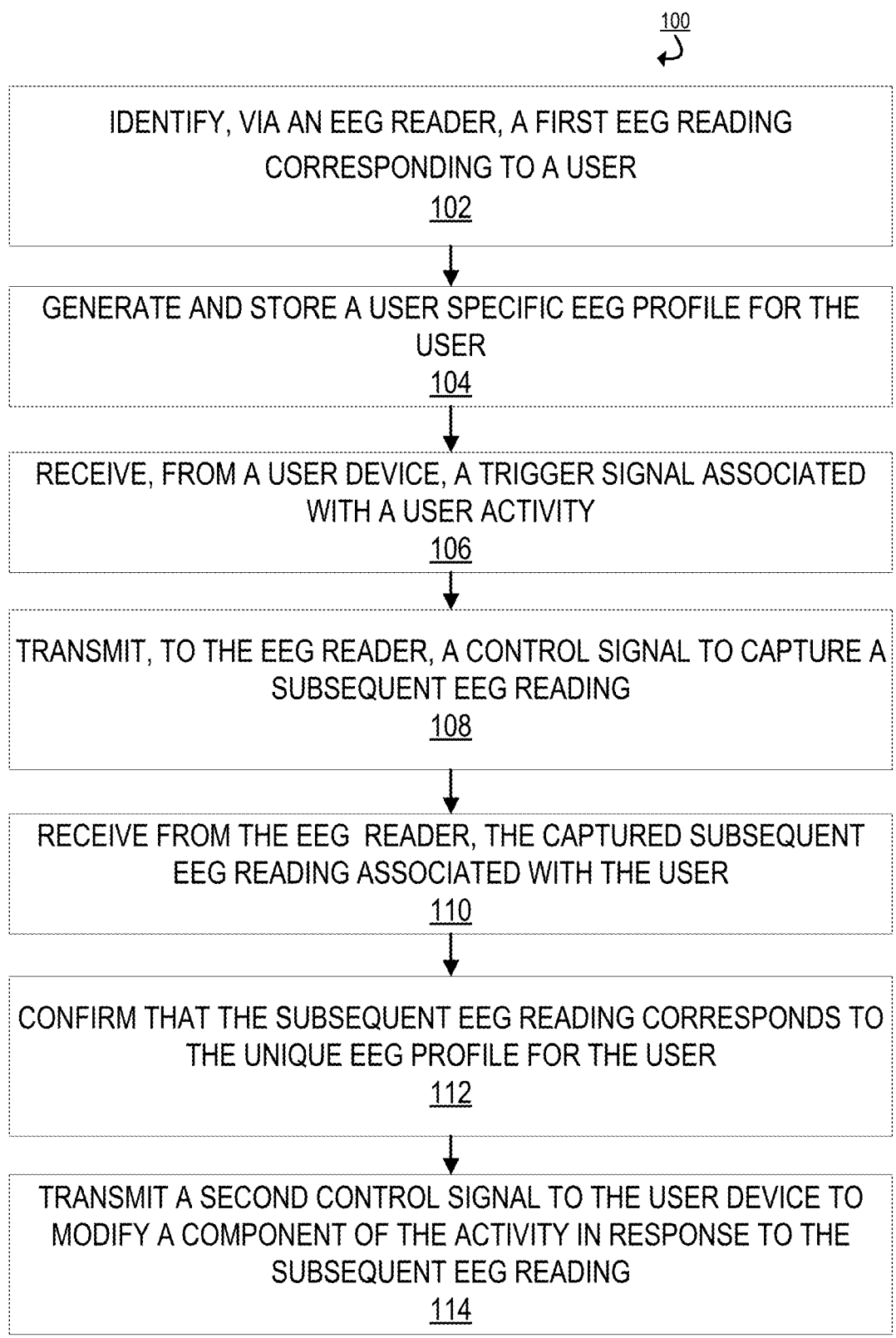
Figure 3:
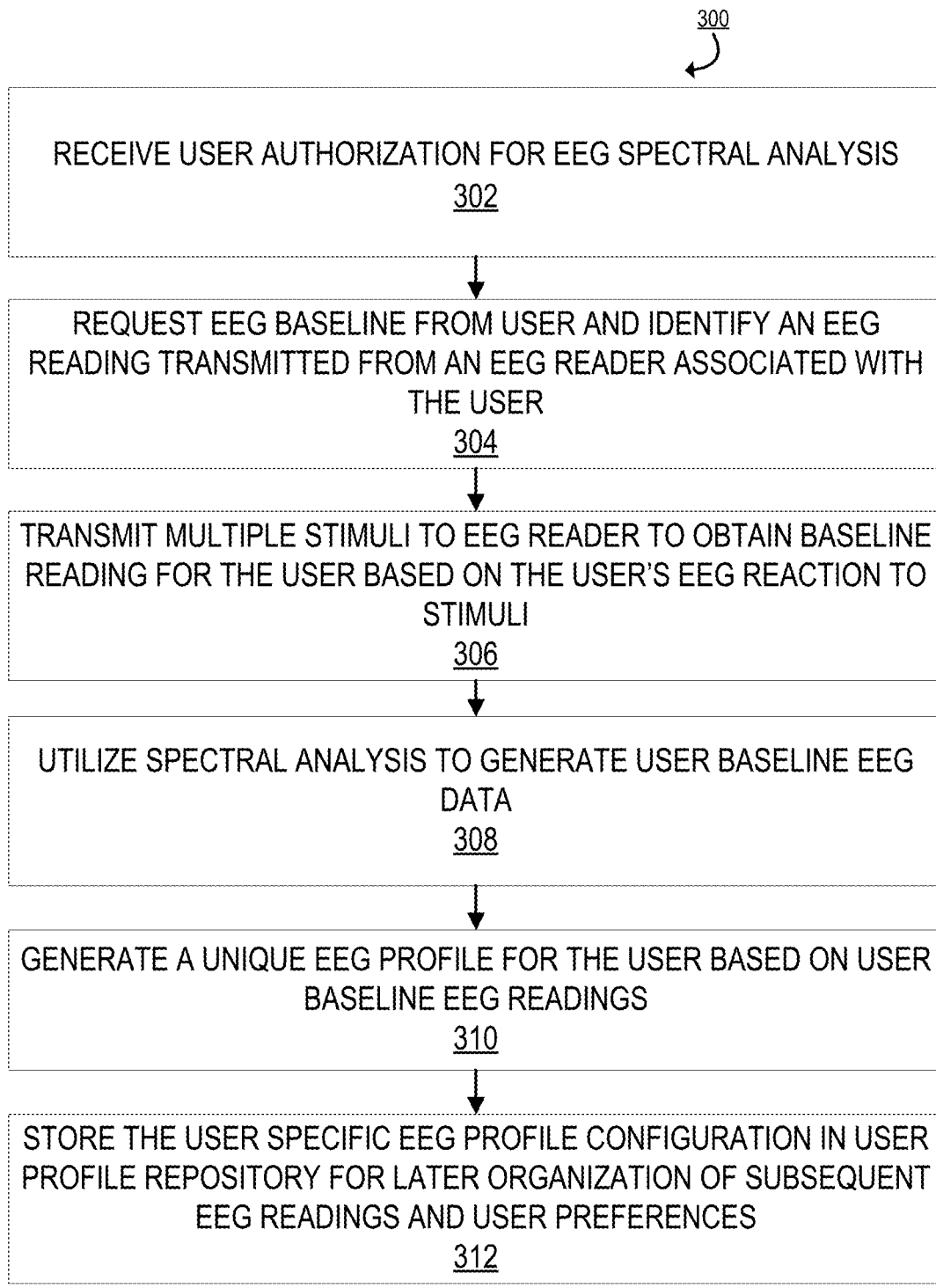
Figure 4:
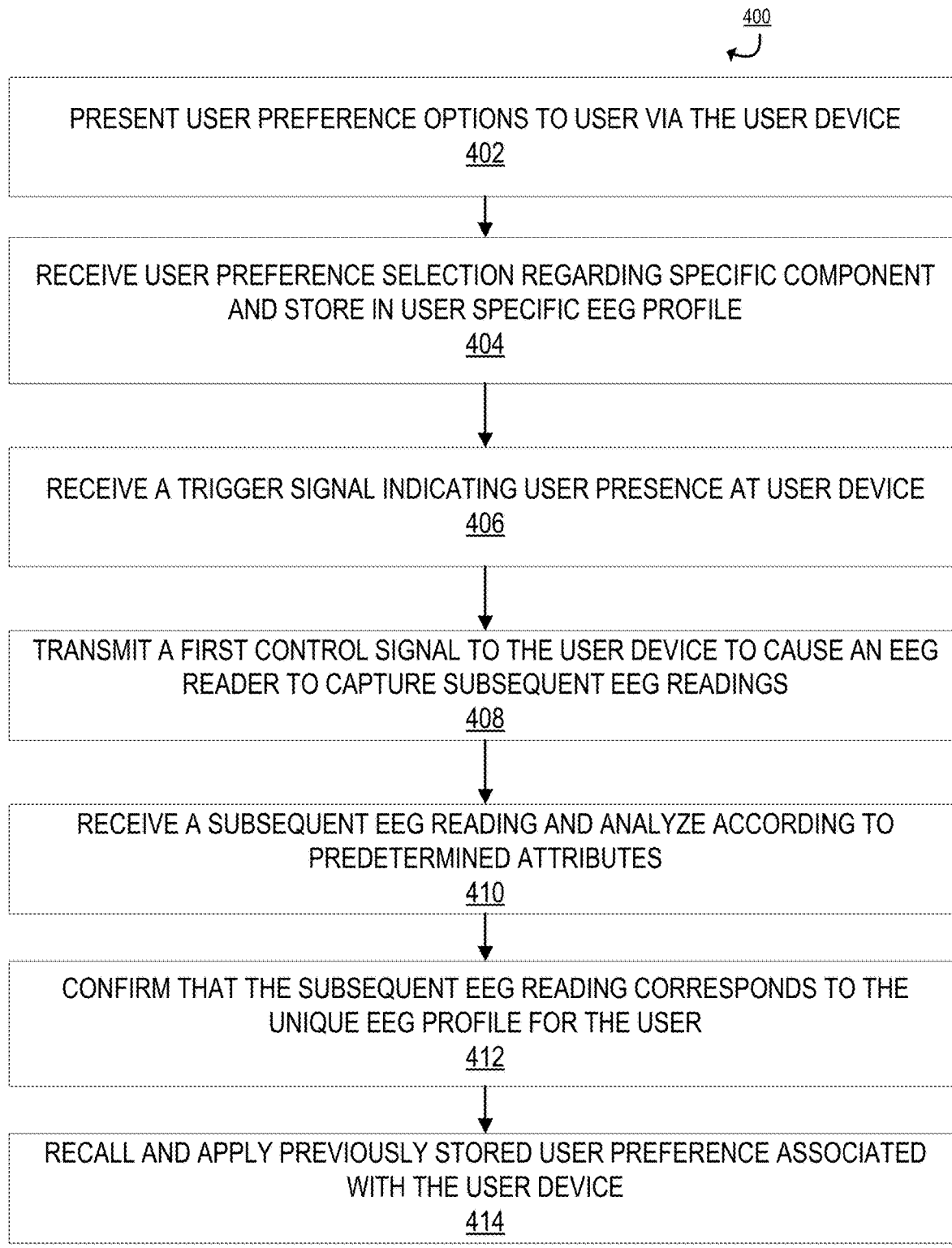
Figure 5:
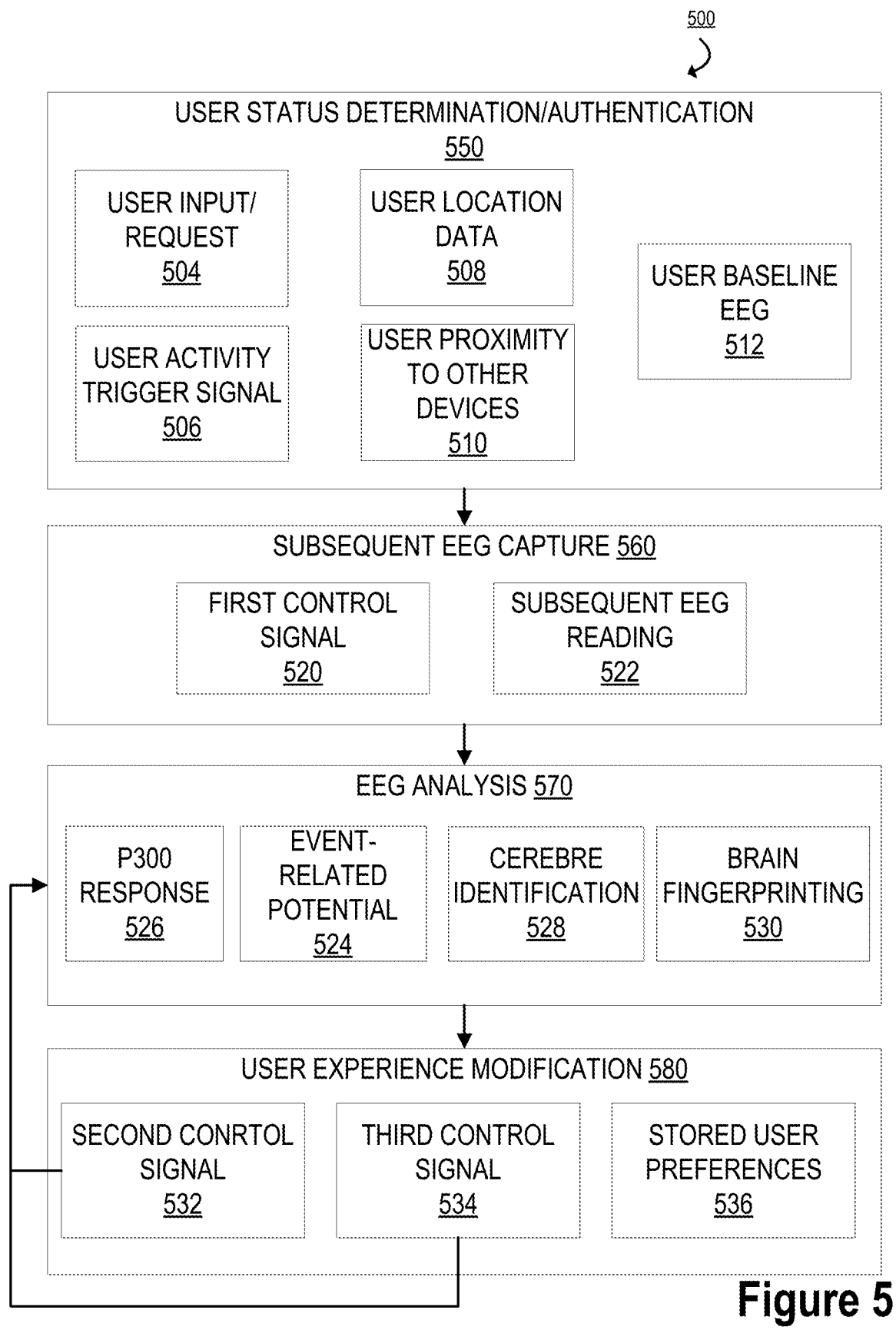

Having thus described embodiments of the invention in general terms, reference will now be made to the accompanying drawings, where:

FIG. 1 illustrates an EEG experience management system environment, in accordance with embodiments of the present invention;

FIG. 2 illustrates a high level flowchart of system interaction within the EEG experience management system environment in accordance with embodiments of the present invention;

FIG. 3 illustrates a high level flowchart of generation and storage of user baseline EEG readings within the EEG experience management system environment, in accordance with embodiments of the present invention;

FIG. 4 illustrates a high level flowchart of the storage and application of user preferences within the EEG experience management system environment, in accordance with embodiments of the present invention; and FIG. 5 illustrates a process for user status determination, EEG capture/analysis, and user experience modification in accordance with embodiments of the present invention.

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on." Like numbers refer to like elements throughout. Additionally, many details that are well known in the art are neither shown nor described.

In some embodiments, an "entity" may be a financial institution or third party merchant. For the purposes of this invention, a "financial institution" may be defined as any organization, entity, or the like in the business of moving, investing, or lending money, dealing in financial instruments, or providing financial services. This may include commercial banks, thrifts, federal and state savings banks, savings and loan associations, credit unions, investment companies, insurance companies and the like. In some embodiments, the entity may allow a user to establish an account with the entity. An "account" may be the relationship that the user has with the entity. Examples of accounts include a deposit account, such as a transactional account (e.g., a banking account), a savings account, an investment account, a money market account, a time deposit, a demand deposit, a pre-paid account, a credit account, or the like. The account is associated with and/or maintained by the entity. In other embodiments, an entity may not be a financial institution. In still other embodiments, the entity may be the merchant itself.

Embodiments of the invention generate a user baseline EEG reading. Using this baseline EEG reading the system may match the user at a third party location to adjust the user experience at that location. The combined use of the P300 type response analysis, CEREBRE protocol biometric information, and stored user preferences determine if a confidence match between the baseline EEG reading of the user and the EEG reading of the user at the location. For example, the user may enter a theater and sit down. The third party theater system may take an EEG reading of the user and transmit the reading to the system. The system may identify the EEG reading as being associated with the user, identify the user's preferences at the theater, and transmit a signal back to the third party system to modify the theater seats or the like to the user preferences. As such, the invention interconnects with a network for real-time data transfer from user devices, third party systems, and other connected devices to receive, analyze, and react to EEG data from an EEG reader.

As such, upon recognition and analysis of EEG data, the system may form and modify a user specific experience via integration within a smart system, third party system, or user device. EEG data can be segmented and sorted based on a time span associated with a known stimulus or event, including, but not limited to, visual or auditory stimuli, or some other, more complex processing of various stimuli. In doing so, the system achieves a design-for-one approach whereby user experiences can vary widely from user to user.

EEG measures voltage fluctuations resulting from ionic current within the neurons of the brain, and in clinical contexts, EEG refers to the recording of the brain's spontaneous electrical activity over a period of time. EEG has very high temporal resolution, on the order of milliseconds, and EEG signals are commonly recorded at sampling rates between 250 and 2000 Hz in clinical and research settings, while modern EEG data collection systems are capable of recording at sampling rates even above 20,000 Hz if so desired. EEG is relatively tolerant of subject movement, unlike most other neuroimaging techniques, and operation of EEG devices is silent, allowing for study of responses to auditory stimuli without the introduction of noise into the EEG signal. Detection of cover brain processing is possible with EEG, meaning that processing does not require a physical response to be registered by an EEG system and allowing for the use of EEG by users who are incapable of making a motor response.

In some embodiments, the invention relates to a system that utilizes a brain computer interface (BCI), or a direct communication pathway between an enhanced or wired brain and an external device. EEG is a monitoring method to record electrical activity of the brain, and is one of the most studied non-invasive approaches to brain computer interfacing, mainly due to its fine temporal resolution, ease of use, portability, and low set-up cost.

EEG data can be segmented and analyzed based on a specific time span associated with a known stimulus or event, and diagnostic applications generally focus on either event-related potentials (ERPs), some variation thereof, or on the spectral content of EEG. Data that is time-locked to complex processing of various stimuli may be referred to as an ERP, while a subclass of the EEG technique also include evoked potentials, or time-locked averages of EEG activity associated with presentation of a specific stimulus of some sort (e.g. auditory, visual, or somatosensory). The invention may use spectral analysis as a method for the study of EEG signals, which specifically involves the study of neural oscillations, more commonly known as "brain waves," that can be observed in EEG signals in the frequency domain. Through statistical analysis and signal processing, the frequency content of EEG signals can be characterized, and periodicities can be detected in the data by observing peaks at the sequences corresponding to these periodicities. Determining what component frequencies are present in a specific user EEG response may involve computing a Fourier transform of a sampled user EEG signal. One can then resynthesize the sampled user EEG signal or compare subsequent signal analysis to detect similarities.

One variation of ERP that the invention may involve is known as the P300 response. The P300 is characterized as a "late" potential, as it occurs at 300-800 milliseconds after the associated stimulus. P300 refers to the electrically positive character of the response as well as the latency of greater than or equal to 300 milliseconds. The P300 may either be a unitary response or a part of a larger grouping of several responses such as the memory and encoding related multifaceted electroencephalographic response, or P300-

MERMER. Embodiments of the present invention utilize one or more of these responses in order to establish an objective method of brain fingerprinting, wherein brain responses to known stimuli are detected, quantified, and analyzed to determine whether or not a user has knowledge of critical information.

In some embodiments, the invention utilizes an averaged ERP to provide accurate biometric information. One such method, known as the cognitive event-related biometric recognition (CEREBRE) protocol, may identify a user accurately by utilizing individually unique responses from multiple functional brain systems, such as the primary visual, facial recognition, and gustatory/appetitive systems. Some embodiments of the invention may incorporate such methods in order to identify users with a high degree of accuracy, and may associate this identification information with a larger profile on the user that contains stored user preferences. The combined use of the P300 type response analysis, CEREBRE protocol biometric information, and stored user preference and user information allows embodiments of the invention to build a user profile for user preferences at one or more locations. The invention may react to this known user information according to a set protocol or operator instructions to modify the user's experience based on a number of factors depending on the capabilities of the user device, third party system, or smart device with which the invention is interfacing.

In some embodiments, the invention generates a user specific EEG profile in a user profile repository using EEG data collected from a user device containing an EEG reader. User specific EEG profile data is collected via a network and stored as a database of ERPs or evoked potentials corresponding to specific sets of stimuli, events, or triggers. In this way, the invention interconnects with a network for real-time data transfer from user devices, third party systems, and other connected devices to receive, analyze, and react to EEG data from an EEG reader to allow generation of a determined user status within a user network account to trigger modification and management of a user experience based on real time EEG data and user specific EEG profile data. In some embodiments, the user status may not be formally known to the user and may only be enacted when an institution confirms an external event is occurring or stimulus is present. When the status is enabled, the system may form and activate a first control signal to cause the EEG reader to capture subsequent EEG readings and react accordingly.

Furthermore, in some embodiments, the system may generate a user baseline reading for storage in the user specific EEG configuration by transmitting a baseline stimulus to the user and recording the user's response received from the EEG reader. This baseline EEG reading can be used for later comparison to subsequent EEG readings in order to identify the user. The EEG reading corresponding to the baseline stimulus is stored in the user specific EEG configuration for the user and predetermined attributes of the EEG reading are analyzed and stored in the EEG experience management system database. The EEG experience management system analyzes predetermined attributes corresponding to the baseline EEG reading and stores the results as a user baseline reading in the user specific configuration.

The EEG experience management system may further develop the user specific EEG configuration corresponding to the user by analyzing predetermined attributes of the subsequent EEG signals and storing them as ERPs or evoked-potentials known to be associated with a particular user response. Analysis of the predetermined attributes of subsequent EEG readings may also allow the system to determine a user response based on a similarity between the analysis results and the same predetermined attributes for a known response. In this way, information received from the EEG reader can be used to determine when the user is present at a certain location, third party system, smart system, or user device, and the subsequent EEG signals can be further analyzed against prior recorded ERPs to determine other attributes of the user's experience.

For example, a user may log on to an online customer portal using a mobile device, said mobile device containing an EEG reader, also known to those of ordinary skill in the art as an electroencephalograph. According to the EEG readings received by the system from the EEG reader, the system may identify the user's presence via a trigger signal associated with a user activity initiated by the user, or by comparing the initial EEG reading with predetermined attributes associated with the baseline EEG reading for the user, and call up the user specific EEG configuration that corresponds to the user. The system may, in some embodiments, modify the information displayed on the user's mobile device based on the user's predetermined preferences or in response to a perceived ERPs previously characterized as indicating a user's reaction based on the predetermined attributes associated with the ERP. The ERP may be previously characterized as indicating the user's familiarity with known stimuli.

In some embodiments, system may identify the user as being within the geographic location based on location data received by the user's device, and associate third party systems, smart systems, and other connected user devices known to be in the same location. The system coordinates with third party systems, smart systems, and user devices, sending control signals in response to subsequent EEG readings and user defined preferences. The system may, in some embodiments, customize specific attributes of the user device in response to EEG signals received by the system and determined to indicate a positive or negative user response. In doing so, the system may transmit a second control signal to the user device wherein the second control signal is configured to modify a component of the activity device at the user's location in response to the subsequent EEG reading.

In some embodiments, the system may further monitor the user's response to the modification of activity device components by receiving a subsequent EEG reading from the user device, analyzing predetermined attributes of the subsequent EEG reading and determining that that the predetermined attributes of the subsequent EEG reading correspond to predetermined attributes known to indicate a positive or negative response. After determining that the subsequent EEG reading indicates a positive or negative response, the system may react accordingly by sending a third control signal to the user device wherein the third control signal is configured to further modify the component of the activity device at the user's location in response to the subsequent EEG reading. This process may be frequently and continuously repeated in order to achieve real time management of the user's experience.

In some embodiments, the system may further monitor the user's response to the modification to activity device components by receiving a subsequent EEG reading from the user device, analyzing predetermined attributes of the subsequent EEG reading and determining that that the user response is positive or negative. The system may then record and store this information as an evoked potential in the user specific EEG configuration as data associated with the user's experience corresponding to a particular variable, such as, but not limited to, a contemporaneous event, a stimulus, a trigger, a modification to the user device, or the like. The system may then generate a report consisting of the ERP and evoked potential data for the particular user, providing an unbiased quantitative report of the user's experience corresponding to the event associated with the evoked potential. The ERP may be previously characterized as indicating the user's familiarity with known stimuli. Upon recognizing that the subsequent EEG reading indicates user familiarity with the known stimuli, the system may generate an alert or response.

In some embodiments, the system may further include recognition of a second user, who may be located in the same location as the first, wherein the system identifies the second user, generates a user specific configuration for the second user, and responds to the second user's EEG readings by transmitting one or more control signals in order to modify the second user's experience. For instance, the system may recognize that there are multiple users located in a vehicle containing one or more EEG readers and which incorporates a smart device designed to interface with the system of the invention. The vehicle may contain a dual zone temperature setting, wherein one zone corresponds to each user. Based on the EEG readings received, the system may recognize that there are two user's present in the proximity of the smart device, and subsequently transmit a series of control signals to adjust discrete temperature settings in each zone according to stored user preferences and the characteristics of the EEG signals received from the users.

Additionally, the system may utilize the artificial intelligence engine in combination with various biometric data received by the system to establish a level of confidence that the user is experiencing discomfort with the current temperature setting of the smart device in the dual zone vehicle. By establishing that the user is experiencing discomfort, the system may then further modify the temperature setting for the zone of the user to another previously stored temperature setting by the user, or a setting that the system determines would be appropriate given a number of other factors such as the real time temperature data for the user's location, the user's previous activities/habits, or the user's preferences as established by previous biometric trigger events.

FIG. 1 illustrates an EEG experience management system environment 200, in accordance with embodiments of the present invention. FIG. 1 provides the system environment 200 for which the EEG experience management system interfaces with users and devices. FIG. 1 provides a unique system that includes specialized servers and system communicably linked across a distributive network of nodes required to perform the functions of recording, modifying and managing device user experiences in response to EEG data and set user preferences.

As illustrated in FIG. 1, the EEG experience management system 208 is operatively coupled, via a network 201 to the user device 204, third party system 205, and to smart system 207. In this way, the EEG experience management system 208 can send information to and receive information from the user device 204, third party system 205, and smart system 207. FIG. 1 illustrates only one example of an embodiment of the system environment 200, and it will be appreciated that in other embodiments one or more of the systems, devices, or servers may be combined into a single system, device, or server, or be made up of multiple systems, devices, or servers.

The network 201 may be a system specific distributive network receiving and distributing specific network feeds and identifying specific network associated triggers. The network 201 may also be a global area network (GAN), such as the Internet, a wide area network (WAN), a local area network (LAN), or any other type of network or combination of networks. The network 201 may provide for wireline, wireless, or a combination wireline and wireless communication between devices on the network 201.

In some embodiments, the user 202 is one or more individuals receiving or transmitting data from the EEG experience management system 208 based on the user's preferences, location, or proximity to one or more of the third party system 205 or smart system 207. FIG. 1 also illustrates a user device 204. The user device 204 may be, for example, a desktop personal computer, business computer, business system, business server, business network, a mobile system, such as a cellular phone, smart phone, personal data assistant (PDA), laptop, or the like. The user device 204 generally comprises a communication device 212, a processing device 214, a memory device 216, an EEG reader 224, and a global positioning system (GPS) device 226. The EEG reader 224 may be physically attached to the user device 204, or may be physically separate from the user device 204 and wireless connected to the user device 204 and/or the network 201. The processing device 214 is operatively coupled to the communication device 212 and the memory device 216. The processing device 214 uses the communication device 212 to communicate with the network 201 and other devices on the network 201, such as, but not limited to the third party system 205, and the smart system 207. As such, the communication device 212 generally comprises a modem, server, or other device for communicating with other devices on the network 201. Other devices such as the third party system 205 and smart system 207 could also be associated with an EEG reader that functions in the same or similar fashion as the EEG reader 224 described above.

The user device 204 comprises computer-readable instructions 220 and data storage 218 stored in the memory device 216, which in one embodiment includes the computer-readable instructions 220 of a user application 222. In some embodiments, the user application 222 allows a user 202 to set up marker codes and communicate with third party system 205, and smart system 207.

As further illustrated in FIG. 1, the EEG experience management system 208 generally comprises a communication device 246, a processing device 248, and a memory device 250. As used herein, the term "processing device" generally includes circuitry used for implementing the communication and/or logic functions of the particular system. For example, a processing device may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. The processing device may include functionality to operate one or more software programs based on computer-readable instructions thereof, which may be stored in a memory device.

The processing device 248 is operatively coupled to the communication device 246 and the memory device 250. The processing device 248 uses the communication device 246 to communicate with the network 201 and other devices on the network 201, such as, but not limited to the third party system 205, smart system 207, and the user device 204. As such, the communication device 246 generally comprises a modem, server, or other device for communicating with other devices on the network 201.

As further illustrated in FIG. 1, the EEG experience management system 208 comprises computer-readable instructions 254 stored in the memory device 250, which in one embodiment includes the computer-readable instructions 254 of an application 258. In some embodiments, the memory device 250 includes data storage 252 for storing data related to the system environment 200, but not limited to data created and/or used by the application 258. Data storage 252 also includes a user profile repository 260 for storing a number a user specific EEG profile 261 for the user 202. In some embodiments, the user specific EEG profile contains data related to EEG readings produced by the EEG reader 224, but may also contain data related to the spectral analysis of EEG readings as well as temporal data, data related to known stimuli, and user preference data for aspects of the user device 204, third party system 205, and smart system 207.

In one embodiment of the EEG experience management system 208, the memory device 250 stores an application 258. Furthermore, the EEG experience management system 208, using the processing device 248 codes certain communication functions described herein. In one embodiment, the computer-executable program code of an application associated with the application 258 may also instruct the processing device 248 to perform certain logic, data processing, and data storing functions of the application. The processing device 248 is configured to use the communication device 246 to communicate with and ascertain data from one or more of the third party system 205, smart system 207, and/or the user device 204.

As illustrated in FIG. 1, the smart system 207 is connected to the EEG experience management system 208, user device 204, and third party system 205. The smart systems 207 has the same or similar components as described above with respect to the user device 204. A smart system 207 may be associated with a third party system or third party system 205 and be able to receive communication and directions for adjustment of the user experience based on the EEG reading. The smart system 207 may include lighting adjustments, sound adjustments, comfort level adjustments, screen modifications, or the like at a third party location.

As illustrated in FIG. 1, the EEG experience management system 208 is connected to the third party system 205, user device 204, and smart system 207. The EEG experience management system 208 has the same or similar components as described above with respect to the user device 204 and smart system 207.

It is understood that the servers, systems, and devices described herein illustrate one embodiment of the invention. It is further understood that one or more of the servers, systems, and devices can be combined in other embodiments and still function in the same or similar way as the embodiments described herein. The EEG experience management system 208 may generally include a processing device communicably coupled to devices as a memory device, output devices, input devices, a network interface, a power source, one or more chips, and the like. The EEG experience management system 208 may also include a memory device operatively coupled to the processing device. As used herein, memory may include any computer readable medium configured to store data, code, or other information. The memory device may include volatile memory, such as volatile Random Access Memory (RAM) including a cache area for the temporary storage of data. The memory device may also include non-volatile memory, which can be embedded and/or may be removable. The non-volatile memory may additionally or alternatively include an electrically erasable programmable read-only memory (EEPROM), flash memory or the like. The memory device may store any of a number of applications or programs which comprise computer-executable instructions/code executed by the processing device to implement the functions of the EEG experience management system 208 described herein.

The user device 204 is configured to transmit a trigger signal via network 201 to the EEG experience management system 208 indicating some activity by user 202. Activity by the user 202 may be related to the use of the user device, or may be related to the user's proximity to the third party system 205, and/or smart system 207. User proximity may be determined using location data from the user device 204 and location data may be obtained from the GPS device 226. In response to the trigger signal, the EEG experience management system 208 can transmit a first control signal to the user device 204 structured to cause the EEG reader 224 to begin capturing subsequent EEG readings for the user 202.

Upon receiving EEG readings from an EEG reader, the EEG experience management system 208 is configured to analyze spectral components of the EEG readings and store the results of the spectral analysis in the user specific EEG profile 261 located in the user profile repository 260. The user specific EEG profile 261 may contain data related to spectral content of EEG readings and may associate the spectral content with data representing known stimuli. EEG readings may also contain temporal data relating to the time at which the readings were recorded by an EEG reader. Association of EEG readings, spectral content, data representing known stimuli and temporal data allows the EEG experience management system 208 to build a library of event-related potentials (ERPs) and baseline EEG readings associated with the user 202 response to known stimuli.

Furthermore, in some embodiments, the system may generate a user baseline reading for storage in the user specific EEG configuration 261 by transmitting a baseline stimulus to the user 202 and recording the user's 202 response received from the EEG reader 224. This baseline EEG reading can be used for later comparison to subsequent EEG readings in order to identify the user 202. The EEG reading corresponding to the baseline stimulus is stored in the user specific EEG configuration 261 for the user and predetermined attributes of the spectral content of the EEG reading are analyzed and stored in the user specific EEG configuration 261. The EEG experience management system 208 analyzes predetermined attributes corresponding to the baseline EEG reading and stores the results as a user baseline reading in the user specific EEG configuration 261.

Spectral analysis of subsequent EEG readings may be compared with stored data in the user specific EEG configuration 261 to determine if predetermined attributes of the spectral data associated with the subsequent readings match previously stored baseline EEG readings. In this way, the EEG experience management system 208 may confirm that the user 202 is present at the user device 204. The baseline EEG reading may have one or more variations due to various stimuli being introduced to the user during generation of the baseline EEG reading. The combined use of the P300 type response analysis, CEREBRE protocol biometric information, and stored user preferences determine the confidence a match exists between the baseline EEG reading of the user and the EEG reading of the user at the authentication location. The EEG experience management system 208 may then request location data from the user device 204, which may be determined by an embedded device such as GPS device 226, or may be provided via access to location data calculated and stored on the user device, such as through the user device 204 location services preferences.

The EEG experience management system may further develop the user specific EEG configuration 261 corresponding to the user 202 by analyzing predetermined attributes of the subsequent EEG signals and storing them as ERPs known to be associated with a particular user response. Analysis of predetermined attributes of the spectral content of the subsequent EEG readings may also allow the system to determine a user response based on a similarity between the analysis results and the same predetermined attributes for a known response. In this way, information received from an EEG reader can be used to determine when the user is present at a certain location, third party system 205, smart system 207, and the subsequent EEG signals can be further analyzed against prior recorded ERPs to determine other attributes of the user's experience.

In some embodiments, EEG experience management system comprises an artificial intelligence engine 262 that is configured to analyze typical user behavior and learn new behaviors of the user and may further develop the user specific configuration 261. The engine may further be able to identify biometric trigger events and user condition based on deviation from typical and learned user behaviors using feedback from one or more biometric sensors that may be located in the user device or a standalone biometric device. In some instances, engine may further be able to identify biometric trigger events and user conditions based on learned user behaviors of other secondary users that are similar to the user. Biometric data may be received by the system from a number of different sources via network 201, including, but not limited to, biometric monitoring devices 206, cameras and sensors embedded in user device 204, user activity history, and analytics data regarding user browsing or spending habits.

The artificial intelligence engine 262 may further comprise the ability to adjust user preference data in real time in response to user behavior such that the information displayed by the system and control signals transmitted by the system modify user devices in response to the user's behaviors. Through use of the artificial intelligence engine, the system may determine a level of confidence that the user is exhibiting a specific emotional response to presented visual stimuli, auditory stimuli, or other known stimuli and respond accordingly. For instance, the system's artificial intelligence engine may interpret a number of data points regarding the user's behavior by using EEG data and biometric trigger events to determine that the user is likely experiencing frustration in response to an offer presented by the system. The system could then note this response in the user specific EEG configuration 261 and utilize the artificial intelligence engine 262 to tailor future interaction between the system and the user in accordance with the user's likes and dislikes.

In some embodiments, the EEG experience management system 208 is configured to recall user specific EEG configuration 261 data and send a second control signal to the user device 204, third party system 205, and/or smart system 207. The second control signal may be followed by a series of other control signals (e.g. third, fourth, or the like) until a desired result is achieved. These subsequent control signals may be designed to modify the third party system 205, and/or smart system 207 in order to cause a change in the user's 202 experience associated with the third party system 205, and/or smart system 207. One way in which a change in the experience may be achieved is by modifying the third party system 205 and/or smart system 207 to present a known stimulus to the user 202. The system may concurrently monitor readings from an EEG reader and analyze spectral components of the subsequent EEG readings for predetermined attributes associated with the user's 202 experience.

The EEG experience management system 208 may recognize subsequent EEG readings as containing spectral components similar to previously recorded EEG readings labeled as specific ERPs indicating user knowledge or familiarity with specific known stimuli or events. In further embodiments of the EEG experience management system 208 may send subsequent control signals to the user device 204, third party system 205, and smart system 207 based on the recognition that an EEG readings for the user 202 match a specific ERP data indicating knowledge of a known stimulus or event. The subsequent control signals may alter the third party system 205, and smart system 207 based on the ERP data received by the system, and/or according to user preferences previously stored in the user specific EEG configuration 261 associated with the specific device or system being modified.

FIG. 2 illustrates a high level flowchart of system interaction process within the EEG experience management system environment 100, in accordance with embodiments of the present invention. As illustrated in block 102, the process 100 is initiated by identifying, via an EEG reader, a first EEG reading corresponding to a user. In some embodiments, the EEG reader is physically connected to the user device. However, the EEG reader may be a separate device in other embodiments that is operatively linked to the user device via a wired or wireless connection of some sort to transfer EEG data from the EEG reader to the user device. The EEG experience management system 208 identifies the first EEG reading by receiving the data associated with the first EEG reading from the EEG reader over the network 201. The EEG experience management system 208 is configured to recognize EEG readings from the EEG reader and analyze the spectral content of these reading in order to match the predetermined attributes of the spectral content of the EEG signal with an existing user specific EEG configuration, or for storage to a newly generated user specific EEG configuration. In some embodiments, the first EEG reading is utilized to map the user's baseline EEG reading.

Next, in block 104, the system generates and stores a user specific EEG configuration for the user 202. Creation of the user specific EEG configuration allows the system to sort EEG data received by the system based on association with a specific user 202 or user device. Generation of the user specific EEG configuration may also include requesting an EEG baseline from the user and transmitting multiple known stimuli to the user device to obtain the user's EEG reaction to the known stimuli. The system may analyze spectral components of the user baseline EEG readings and store them in the user specific EEG configuration, as further described in FIG. 3.

Next, in block 106, the system receives a trigger signal associated with a user activity. The trigger signal can be any signal indicating that the user 202 is using the user device or performing some activity at a third party system. In some embodiments, the trigger signal may be further limited to include only activities associated with a certain application or function of the user device. In some embodiments, the trigger signal may be associated with an activity that the user 202 or a system administrator has labeled as a trigger activity. In still other embodiments, the trigger signal may be associated with the user's location in proximity to other devices or systems, such as the third party system, and smart system. Furthermore, the trigger signal could be an EEG reading captured by the EEG reader and registered by the system as indicating user activity based on the spectral content of the EEG reading.

Next, as illustrated in block 108, the process 100 continues by transmitting a control signal to the EEG reader to cause the EEG reader to capture and communicate subsequent EEG readings for the user. The EEG reader is instructed to transfer EEG readings associated with the user 202 to the EEG experience management system via the network. The EEG readings are captured as a consistent stream of EEG data and can be later segmented according to the time at which they were captured or received by the system. This temporal recognition of EEG data captured by the EEG reader is used to associate specific EEG frequency data with known stimuli or events.

Next, as illustrated in block 110, the system receives the captured subsequent EEG readings associated with the user. Subsequent EEG readings are analyzed according to their spectral components and predetermined attributes of the spectral components are used to confirm that the subsequent reading corresponds to the unique EEG configuration for a specific user, as shown in block 112. The combined use of the P300 type response analysis, CEREBRE protocol biometric information, and stored user preference determine if a confidence match exits between the baseline EEG reading of the user and the EEG reading of the user. Once the specific user is determined, the user specific EEG configuration for that user can be loaded by the EEG experience management system. The user specific EEG configuration contains user preference data and any previously recorded ERP data associated with the specific user. These user preferences and previously recorded ERPs may be utilized by the system in generating a control signal for modifying the user's experience regarding the user device or some other device, such as the third party system and/or the smart system.

Finally, as illustrated in block 114, the system transmits a control signal to the user device, third party systems, or smart devices to modify one or more component in response to the subsequent EEG reading. The control signal varies based on the component of the device that is being modified, and may include instructions for adjustments of a wide range of parameters that alter the user's experience, including, but not limited to, a display of some visual stimuli, a generated auditory stimuli, an adjustment to a smart home device such as a thermostat or lighting fixture, or the like. In the case of the third party systems or smart devices, the control signal may alter a device that the user may or may not be actively interacting with. As an example, the control signal may be generated in response to the subsequent EEG reading that the system recognizes as sharing the same predetermined spectral attributes as an ERP indicating a particular user desire. The control signal may be configured to alter, for instance, the position or firmness of a smart movie theater seat that the system recognizes the user 202 is sitting in by recognition of location or paired device data from the user device.

FIG. 3 illustrates a high level flowchart of the generation and storage of user baseline EEG readings within the EEG experience management system environment 300, in accordance with one embodiment of the invention. As illustrated in block 302, the process 300 is initiated by receiving authorization from the user 202 for spectral analysis of EEG signals. In some embodiments, this authorization is needed before the system begins analyzing the frequency content of EEG readings from a user device 204, and is obtained from the user 202 prior to the creation of a user specific EEG configuration for storage of subsequent EEG readings and analysis results. In some embodiments, the system sends a prompt to the user 202 via the user device 204 requesting authorization for the system to perform analyze and store EEG data received from the user 202 via EEG reader.

After authorization for spectral analysis, as illustrated in block 304, the system requests from the user 202 an EEG baseline reading and begins to identify EEG signals received from the EEG reader as being associated with the specific user 202. The user 202 can then accept the request for the system to initiate the process for forming a baseline EEG reading associated with the user 202. In some embodiments, the baseline reading for the user may include a number of ERPs associated with known stimuli presented to the user via the user device. In other embodiments, the baseline reading may be measured as a specific ERP type response such as a P300 response, or late potential at a time interval beyond 300 milliseconds after the presentation of a known stimuli. In further embodiments, the user baseline EEG readings may be characterized according to the cognitive event-related biometric recognition (CEREBRE) protocol by utilizing individually unique responses from multiple functional brain systems, such as the primary visual, facial recognition, and gustatory/appetitive systems.

Based on the type of user baseline EEG the system utilizes in a particular embodiment, the system then transmits multiple stimuli to the EEG reader to obtain baseline EEG readings for the user based on the user's EEG response to the multiple stimuli, as shown in block 306. The multiple stimuli are designed to generate a reaction from the user that is detectable via EEG readings captured after the user 202 is exposed to the stimuli and known to induce detectable ERP frequency attributes that can be analyzed by the system and stored in the user specific EEG configuration. In some embodiments the stimuli may be generated visually on the user device 204, while in other embodiments the stimuli may be generated as auditory signals. Further embodiments may include any stimuli that can be detected by multiple functional brain systems as used in the CEREBRE protocol or other similar biometric recognition techniques involving user specific EEG readings.

Next, as illustrated in block 308, the system utilizes spectral analysis to generate user baseline EEG data from the baseline EEG readings received in response to the multiple stimuli. EEG readings received in response to the multiple stimuli can be segmented and time-locked to the occurrence or presentation of the multiple stimuli, and predetermined attributes of the frequencies observed in the EEG readings can be compiled as user baseline EEG data corresponding the user 202. Specific brain activity responses associated with various functional brain systems are evidenced in the baseline EEG readings by the spectral content in the EEG readings. This data can then be utilized to verify that a user is present, or alternatively verify that the user's experience to subsequent stimuli match the response observed to the baseline stimuli. The baseline EEG reading may have one or more variations due to various stimuli being introduced to the user during generation of the baseline EEG reading. In some embodiments, the user 202 may be asked to rate their response as indicating a particular emotional response, such as contentment or displeasure, thereby allowing the system to associate particular EEG spectral analysis of known stimuli with particular user emotional responses.

Next, as illustrated in block 310, the system may store the generated user baseline EEG data in the newly generated user specific EEG profile. Generation of unique user responses to multiple stimuli and spectral analysis of subsequent EEG readings allows the system to later identify the user 202 and characterize user responses, and the generation of the user specific profile allows a storage location for the system to place new data associated with user activity, user preferences, user device 204 identification information, user location data, and the like. As shown in block 312, the user specific EEG profile is stored in the user profile repository for later reference by the system as it receives EEG readings from user devices.

FIG. 4 illustrates a high level flowchart of the storage and application of user preferences within the EEG experience management system environment 400, in accordance with one embodiment of the invention. As illustrated in block 402, the process 400 is initiated as the system presents the user 202 with user preference options. In some embodiments, the system is configured to present the user 202 with preferences regarding components of the user device 204, a mobile user portal for interaction with an institution, such as the items displayed on a webpage when the user 202 logs into the portal, or various attributes of the third party system and/or the smart system. For example, the user 202 may be presented with user preference options regarding a component setting associated with the smart system 207, such as thermostat temperature settings or the like. In some embodiments, the user is able to set specific user preferences for storage in the user specific EEG configuration.

As illustrated in block 404, the system receives the user preference selections regarding the specific component of the device or system in question and stores the preference in the user specific EEG configuration. This allows the system to later recall the user preferences at any time when the system is interfacing with the user 202.

Next, as illustrated in block 406, the system receives a trigger signal indicating that the user is present at the user device 204. The user device 204 is configured to transmit a trigger signal via network 201 to the system indicating an activity by user 202. Activity by the user 202 may be related to the use of the user device, or may be related to the user's proximity to the third party system, and/or smart system.

Next, as illustrated by block 408, the system transmits a control signal to the EEG reader to cause the EEG reader to capture and communicate subsequent EEG readings for the user. The EEG reader is instructed to transfer EEG readings associated with the user 202 to the system via the network 201. The EEG readings are captured as a consistent stream of EEG data and can be later segmented according to the time at which they were captured or received by the system. This temporal recognition of EEG data captured by the EEG reader is used to associate specific EEG frequency data with known stimuli or events.

Next, as illustrated in block 410, the system receives the captured subsequent EEG readings associated with the user. Subsequent EEG readings are analyzed according to their spectral components and predetermined attributes of the spectral components are used to confirm that the subsequent reading corresponds to the baseline EEG reading of the user stored in the unique EEG configuration for the user. Once the specific user is determined, the user specific EEG configuration for that user can be loaded by the system. The user specific EEG configuration contains user preference data and any previously recorded ERP data associated with the specific user. These user preferences and previously recorded ERPs may be utilized by the system in generating a control signal for modifying the user's experience at the location of the activity.

Subsequent EEG readings are analyzed according to their spectral components and predetermined attributes of the spectral components are used to confirm that the subsequent reading corresponds to the unique EEG configuration for a specific user, as shown in block 412. Once the specific user is determined, the user specific EEG configuration for that user can be integrated at the location of the user and loaded by the system. The user specific EEG configuration contains user preference data associated with the specific user.

Finally, as shown in block 414, the system is configured to recall and apply user preference options selected by user 202 which were previously stored in the user specific EEG configuration. In some embodiments, this control signal may modify the third party system and/or smart system. The control signal varies based on the component of the device that is being modified, and may include instructions for adjustments of a wide range of parameters that alter the user's experience, including, but not limited to, a display of some visual stimuli, a generated auditory stimuli, an adjustment to a smart home device such as a thermostat or lighting fixture, or the like. In the case of the third party system, the control signal may alter a device that the user may or may not be actively interacting with. As an example, the control signal may be generated in response to the subsequent EEG reading that the system recognizes as sharing the same predetermined spectral attributes as an ERP indicating a particular user desire. The control signal may be configured to alter, for instance, the position or firmness of a smart movie theater seat that the system recognizes the user 202 is sitting in by recognition of location or paired device data from the user device.

In some embodiments, the system may utilize other data stores in the user specific EEG configuration, such as data from the system's artificial intelligence engine. The engine may further be able to identify biometric trigger events and user condition based on deviation from typical and learned user behaviors using feedback from one or more biometric sensors in the user device 204 or other biometric devices and store this information in the user specific EEG configuration. In some instances, engine may further be able to identify biometric trigger events and user conditions based on learned user behaviors of other secondary users that are similar to the user. Biometric data may be received by the system from a number of different sources via network 201, including, but not limited to, biometric monitoring sensors, cameras and sensors embedded in user device 204, user activity history, and analytics data regarding user browsing or spending habits. Upon confirmation that the user is present via spectral analysis and matching of EEG readings, the system may utilize user biometric data in conjunction with the artificial intelligence engine in order to alter the user's experience as a response to biometric trigger events.

For instance, one form of a biometric trigger event may be the user's perceived frustration in dealing with a user interface on the user device. The system may utilize the artificial intelligence engine in combination with various biometric data received by the system to establish a level of confidence that the user is experiencing frustration based on various biometric information such as facial recognition, and the like. In response to this biometric trigger event, the system may alter the user interface presented on the user device to exclude the information or stimuli that the system associates with the user's biometric trigger event of frustration. As an example, the user may originally be presented with an offer for a specific product based on data regarding the user's interests or previous browsing history. The system may recognize a biometric trigger event when the user is presented with the offer that indicates user frustration, and subsequently alter the user interface to remove the offer or replace the offer with an offer related to subject matter that the user has responded to in a positive manner or otherwise indicated, by their browsing history, previous activity, or past spending habits, that they have interest in.

Additionally, the system may use biometric trigger events to indicate that the user reacts positively to certain information, and may store this information for later referral when altering the display on a user device or modifying some component of a smart device. Various stimuli that the system presents on the user device or the third party system may be monitored in conjunction with biometric trigger events. The biometric trigger event may indicate that that the user is experiencing a positive response to the various stimuli. For instance, the user may react positively to the presentation of a certain layout upon logging in to a user portal controlled by the system on the user device. The system may recognize and record the biometric triggering event indicating the positive reaction from the user and utilize the artificial intelligence engine to ensure that the system causes the user device to display layouts and content to the user that is tailored to the user's likes and dislikes.

FIG. 5 illustrates a process for user status determination, EEG capture, EEG analysis, and user experience modification 500, in accordance with embodiments of the present invention. As illustrated, FIG. 5 provides a system determination of a user status and analysis of subsequent EEG readings to modify a user experience. As illustrated in block 550, the process is imitated by determining the user's status and authenticating the user. The user status may be determined from user input/request 504, user activity trigger signal 506, user location data 508, user proximity to other devices 510, and comparison of EEG readings with the user baseline EEG 512.

In some embodiments, the system may receive user input/request 504 identifying the user's interaction with the user device, third party system, and/or the smart system. In this way, the user 202 may provide input via the user device or some other device or system to identify their presence at the device or interaction with the system. The user 202 may input via a display on the user device and the input may be communicated to the system via a network.

In some embodiments, the system may utilize a user activity trigger signal 506 to identify the user status as present at the user device, third party system, and to smart system. In this way, the user's actions may passively engage the user device or other device or system to alert the EEG experience management system that the user is performing some activity or is in a certain location.

In some embodiments, the system may utilize user location data 508 or user proximity to other devices 510 as identifying information to trigger user status. In this way, the user may have previously allowed the EEG experience management system permission to use location data from the user device or other device such as the smart system. Location data from these devices may alert the system of the user's status and prompt the EEG experience management system to engage the user or EEG reader.

In some embodiments, the system may be monitoring the user's EEG readings using an EEG reader located on a device separate from the user device. The EEG experience management system may utilize the user baseline EEG reading previously stored in the user specific configuration to match the user's EEG readings and determine that the user is present at a third party system, or smart system. In this way, the system may identify the user without data from the user device, and may load the user specific EEG configuration for the user regardless of whether the user is carrying the user device.

Next, as illustrated in block 560, the process 500 continues through subsequent EEG capture. In this way, the EEG experience management system requests subsequent EEG signals from the EEG reader for later analysis. The system can send a first control signal 520 to the EEG reader in order to prompt the EEG reader to begin sending subsequent EEG readings 522 to the system. In this way, the system can prompt the EEG reader to begin recording and transmitting EEG data to the system via the network upon determining that the user status indicates that the user is able to utilize the system.

Next, as illustrated in block 570, the process 500 continues by analyzing subsequent EEG data received from the EEG reader. The analysis may involve the application of certain spectral analysis protocols or EEG data classifications. EEG readings may be analyzed according the P300 response 526, or classified generally as some type of event-related potential 524. Protocols involving CEREBRE identification 528 or brain fingerprinting 530 may also be employed.

In some embodiments, the subsequent EEG signals may be segmented and analyzed after a 300 millisecond time interval following known stimuli. In this way, the system can analyze the EEG signal as a P300 response 526, which may indicate latent processing of known stimuli. The system may also classify an EEG signal more broadly as an event-related potential 524 by associating the spectral frequency content of the EEG reading with a known stimuli based on time data of when the signal was recorded in relation to the user experiencing the known stimuli.

In some embodiments, the system may employ a specific protocol to identify the user based on spectral analysis of the EEG reading frequency content. The system may use a protocol such as CEREBRE identification 528 by utilizing individually unique responses from multiple functional brain systems, such as the primary visual, facial recognition, and gustatory/appetitive systems. The system may also employ a protocol used for the brain finger printing 530 technique, wherein brain responses to known stimuli are detected, quantified, and analyzed to determine whether or not a user has knowledge of critical information.

Next, as illustrated in block 580, the process 500 continues by user experience modification. In this way, the system may communicate with the user device, third party, and/or smart system through the use of control signals to modify selected components of each device or system based on stored user preferences from the user specific EEG configuration.

In some embodiments, the EEG experience management system may send a series of subsequent control signals to the user device or other device or system, represented in process 500 as blocks 532 and 534. While the Figure only lists two successive control signals, it is understood that the system may employ the use of as many subsequent control signals are necessary to achieve a desired modification of the user's experience. As illustrated, in modifying the user experience, the system may access the user preferences 536 stored in the user specific configuration following the identification of the user based on EEG reading content. In some embodiments, second control signal may modify the user device or other device or system such that the user's EEG reading is expected to change in response. In some embodiments, the system may analyze subsequent EEG readings following the second control signal 532 and determine that the user device or other device or system requires further modification. The system may then transmit the third control signal to modify the user device or other device or system.

As will be appreciated by one of ordinary skill in the art, the present invention may be embodied as an apparatus (including, for example, a system, a machine, a device, a computer program product, and/or the like), as a method (including, for example, a business process, a computer-implemented process, and/or the like), or as any combination of the foregoing. Accordingly, embodiments of the present invention may take the form of an entirely software embodiment (including firmware, resident software, microcode, and the like), an entirely hardware embodiment, or an embodiment combining software and hardware aspects that may generally be referred to herein as a "system." Furthermore, embodiments of the present invention may take the form of a computer program product that includes a computer-readable storage medium having computer-executable program code portions stored therein. As used herein, a processor may be "configured to" perform a certain function in a variety of ways, including, for example, by having one or more special-purpose circuits perform the functions by executing one or more computer-executable program code portions embodied in a computer-readable medium, and/or by having one or more application-specific circuits perform the function. As such, once the software and/or hardware of the claimed invention is implemented the computer device and application-specific circuits associated therewith are deemed specialized computer devices capable of improving technology associated with the in authorization and instant integration of a new credit card to digital wallets.

It will be understood that any suitable computer-readable medium may be utilized. The computer-readable medium may include, but is not limited to, a non-transitory computer-readable medium, such as a tangible electronic, magnetic, optical, infrared, electromagnetic, and/or semiconductor system, apparatus, and/or device. For example, in some embodiments, the non-transitory computer-readable medium includes a tangible medium such as a portable computer diskette, a hard disk, a random access memory (RAM), a read-only memory (ROM), an erasable programmable read-only memory (EPROM or Flash memory), a compact disc read-only memory (CD-ROM), and/or some other tangible optical and/or magnetic storage device. In other embodiments of the present invention, however, the computer-readable medium may be transitory, such as a propagation signal including computer-executable program code portions embodied therein.

It will also be understood that one or more computer-executable program code portions for carrying out the specialized operations of the present invention may be required on the specialized computer include object-oriented, scripted, and/or unscripted programming languages, such as, for example, Java, Perl, Smalltalk, C++, SAS, SQL, Python, Objective C, and/or the like. In some embodiments, the one or more computer-executable program code portions for carrying out operations of embodiments of the present invention are written in conventional procedural programming languages, such as the "C" programming languages and/or similar programming languages. The computer program code may alternatively or additionally be written in one or more multi-paradigm programming languages, such as, for example, F#.

It will further be understood that some embodiments of the present invention are described herein with reference to flowchart illustrations and/or block diagrams of systems, methods, and/or computer program products. It will be understood that each block included in the flowchart illustrations and/or block diagrams, and combinations of blocks included in the flowchart illustrations and/or block diagrams, may be implemented by one or more computer-executable program code portions. These one or more computer-executable program code portions may be provided to a processor of a special purpose computer for the authorization and instant integration of credit cards to a digital wallet, and/or some other programmable data processing apparatus in order to produce a particular machine, such that the one or more computer-executable program code portions, which execute via the processor of the computer and/or other programmable data processing apparatus, create mechanisms for implementing the steps and/or functions represented by the flowchart(s) and/or block diagram block(s).

It will also be understood that the one or more computer-executable program code portions may be stored in a transitory or non-transitory computer-readable medium (e.g., a memory, and the like) that can direct a computer and/or other programmable data processing apparatus to function in a particular manner, such that the computer-executable program code portions stored in the computer-readable medium produce an article of manufacture, including instruction mechanisms which implement the steps and/or functions specified in the flowchart(s) and/or block diagram block(s).

The one or more computer-executable program code portions may also be loaded onto a computer and/or other programmable data processing apparatus to cause a series of operational steps to be performed on the computer and/or other programmable apparatus. In some embodiments, this produces a computer-implemented process such that the one or more computer-executable program code portions which execute on the computer and/or other programmable apparatus provide operational steps to implement the steps specified in the flowchart(s) and/or the functions specified in the block diagram block(s). Alternatively, computer-implemented steps may be combined with operator and/or human-implemented steps in order to carry out an embodiment of the present invention.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

INCORPORATION BY REFERENCE

To supplement the present disclosure, this application further incorporates entirely by reference the following commonly assigned patent applications:

| Docket Number | U.S. Pat. No. | Title | Filed On |
|---|---|---|---|
| 8086US1.014033.3113 | 10,567,961 | SYSTEM FOR ELECTROENCEPHALOGRAM PATTERNING RECOGNITION FOR AUTHENTICATION | Concurrently herewith |
| 8087US1.014033.3114 | 10,456,054 | ELECTROENCEPHALOGRAM TRIGGERED RESOURCE DISTRIBUTION QUERY SYSTEM | Concurrently herewith |

What is claimed is:

1. A system for electroencephalogram (EEG) triggered experience modification, the system comprising:
a memory device with computer-readable program code stored thereon;
a communication device;
an EEG reader;
a processing device operatively coupled to the memory device and the communication device, wherein the processing device is configured to execute the computer-readable program code to:
identify, via the EEG reader, a baseline EEG reading corresponding to a user;
generate a user specific EEG profile for the user based on spectral analysis of a set of predetermined attributes of the baseline EEG reading;
store the user specific EEG profile in a user data repository;
transmit a control signal to a user device causing the user device to display a set of user preferences for experience modification, wherein the user preferences for experience modification comprise preferences for one or more visual or auditory stimuli;
receive selected user preferences and store the selected user preferences in the user data repository;
receive a trigger signal associated with a user activity initiated by the user;
in response to the trigger signal, transmit a second control signal to cause the EEG reader to capture a subsequent EEG reading;
receive, from the EEG reader, the subsequent EEG reading;
confirm that the subsequent EEG reading corresponds to the user specific EEG profile for the user by using a comparative spectral analysis of the subsequent EEG reading and the baseline EEG reading and identifying that predetermined attributes of the subsequent EEG reading match the predetermined attributes of the baseline EEG reading associated with the user;
in response to confirming that the subsequent EEG reading corresponds to the user specific EEG profile, transmit a third control signal to the user device, wherein the third control signal is configured to customize a component of the user device in accordance with the user preferences for experience modification, wherein customizing the component of the user device causes a change in the user's experience, and wherein the user's experience comprises experience of the one or more visual or auditory stimuli;
transmit a fourth control signal to cause the EEG reader to capture a second subsequent EEG reading after the change in the user's experience;
receive, from the EEG reader, the second subsequent EEG reading; and
confirm that the second subsequent EEG reading corresponds to a predetermined user reaction for the user by using a second comparative spectral analysis of the second subsequent EEG reading.

2. The system of claim 1, wherein the third control signal transmitted to the user device is configured to customize the component of the user device in response to the subsequent EEG reading by applying a stored selected user preference associated with the user activity and the user device, wherein the stored selected user preference is one of the stored selected user preferences in the user data repository.

3. The system of claim 1, wherein the processing device is further configured to execute the computer-readable program to:
receive, from the EEG reader, the subsequent EEG reading; and
transmit, to a third party system, a fifth control signal, wherein the fifth control signal is configured to customize a component of the third party system and wherein customizing the component of the third party system changes the user's experience at the third party system.

4. The system of claim 1, wherein generating the user specific EEG profile for the user further comprises:
analyzing frequency content for the baseline EEG reading time-locked to a known event or stimulus;
detecting periodicities, patterns, and component frequencies present in the baseline EEG reading; and
storing the periodicities, patterns, and component frequencies for the baseline EEG reading in the user specific EEG profile.

5. The system of claim 1, wherein performing the comparative spectral analysis of the subsequent EEG reading and the baseline EEG reading further includes comparing predetermined attributes of the baseline EEG reading and the subsequent EEG reading to identify a match or partial match for the user; and
generating a confidence that the subsequent EEG reading is an EEG reading of the user based on a comparative analysis to the baseline EEG reading for the user.

6. The system of claim 1, wherein identifying the baseline EEG reading further comprises recording an EEG signal for the user at a time interval of at least 300 milliseconds after a known event or stimulus.

7. The system of claim 1, wherein the processing device is further configured to execute the computer-readable program code to interface with multiple users at one time; and
transmit a series of control signals to customize discrete components of the user device, a set of user devices, or a smart system in response to subsequent EEG readings for the multiple users, wherein customizing the discrete components causes a change in the experience of each of the multiple users.

8. A computer program product for electroencephalogram (EEG) triggered experience modification with at least one non-transitory computer-readable medium having computer-readable program code portions embodied therein, the computer-readable program code portions comprising:

an executable portion configured to control an EEG reader of a device;

an executable portion configured to identify, via the EEG reader, a baseline EEG reading corresponding to a user;

an executable portion configured to generate a user specific EEG profile for the user based on spectral analysis of a set of predetermined attributes of the baseline EEG reading;

an executable portion configured to transmit the user specific EEG profile for storage to a user data repository;

an executable portion configured to transmit a control signal to a user device causing the user device to display a set of user preferences for experience modification, wherein the user preferences for experience modification comprise preferences for one or more visual or auditory stimuli;

an executable portion configured to receive selected user preferences and store the selected user preferences in the user data repository;

an executable portion configured to receive a trigger signal associated with a user activity initiated by the user;

an executable portion configured to, in response to the trigger signal, transmit a second control signal to cause the EEG reader to capture a subsequent EEG reading;

an executable portion configured to receive, from the EEG reader, the subsequent EEG reading;

an executable portion configured to confirm that the subsequent EEG reading corresponds to the user specific EEG profile for the user by using a comparative spectral analysis of the subsequent EEG reading and the baseline EEG reading and identifying that predetermined attributes of the subsequent EEG reading match the predetermined attributes of the baseline EEG reading associated with the user;

an executable portion configured to, in response to confirming that the subsequent EEG reading corresponds to the user specific EEG profile, transmit a third control signal to the user device, wherein the third control signal is configured to customize a component of the user device in accordance with the user preferences for experience modification, and wherein customizing the component of the user device causes a change in the user's experience, and wherein the user's experience comprises experience of the one or more visual or auditory stimuli;

an executable portion configured to transmit a fourth control signal to cause the EEG reader to capture a second subsequent EEG reading after the change in the user's experience;

an executable portion configured to receive, from the EEG reader, the second subsequent EEG reading; and an executable portion configured to confirm that the second subsequent EEG reading corresponds to a predetermined user reaction for the user by using a second comparative spectral analysis of the second subsequent EEG reading.

9. The computer program product of claim 8, wherein the third control signal transmitted to a device in proximity to the user activity is configured to customize the component of the user device in response to the subsequent EEG reading by applying a stored selected user preference associated with the user activity and the user device, wherein the stored selected user preference is one of the stored selected user preferences in the user data repository.

10. The computer program product of claim 8, further comprising:

an executable portion configured to receive, from the EEG reader, the subsequent EEG reading; and an executable portion configured to transmit, to a third party system, a fifth control signal, wherein the fifth control signal is configured to customize a component of the third party system, and wherein customizing the component of the third party system changes the user's experience at the third party system.

11. The computer program product of claim 8, wherein the executable portion configured to generate the user specific EEG profile for the user further comprises:

an executable portion configured for analyzing frequency content for the baseline EEG reading time-locked to a known event or stimulus;

an executable portion configured for detecting periodicities, patterns, and component frequencies present in the baseline EEG reading; and an executable portion configured for storing the periodicities, patterns, and component frequencies for the baseline EEG reading in the user specific EEG profile.

12. The computer program product of claim 8, wherein performing the comparative spectral analysis of the subsequent EEG reading and the baseline EEG reading further includes comparing predetermined attributes of the baseline EEG reading and the subsequent EEG reading to identify a match or partial match for the user; and generating a confidence that the subsequent EEG reading is an EEG reading of the user based on a comparative analysis to the baseline EEG reading for the user.

13. The computer program product of claim 8, wherein identifying the baseline EEG reading further comprises recording an EEG signal for the user at a time interval of at least 300 milliseconds after a known event or stimulus.

14. The computer program product of claim 8, wherein the computer-readable program code portions further comprise an executable portion configured to interface with multiple users at one time; and an executable portion configured to transmit a series of control signals to customize discrete components of the user device, a set of user devices, or a smart system in response to subsequent EEG readings for the multiple users, wherein customizing the discrete components causes a change in the experience of each of the multiple users.

15. A computer-implemented method for electroencephalogram (EEG) triggered experience modification, the method comprising:

providing a computing system comprising a computer processing device, an EEG reader, and a non-transitory computer readable medium, where the computer readable medium comprises configured computer program instruction code, such that when said instruction code is operated by said computer processing device, said computer processing device performs the following operations:

identifying, via the EEG reader, a baseline EEG reading corresponding to a user;

generating a user specific EEG profile for the user based on spectral analysis of a set of predetermined attributes of the baseline EEG reading;

storing the user specific EEG profile in a user data repository;

transmitting a control signal to a user device causing the user device to display a set of user preferences for experience modification, wherein the user preferences for experience modification comprise preferences for one or more visual or auditory stimuli;

receiving selected user preferences and storing the selected user preferences in the user data repository;

receiving a trigger signal associated with a user activity initiated by the user;

in response to the trigger signal, transmitting a second control signal to cause the EEG reader to capture a subsequent EEG reading;

receiving, from the EEG reader, the subsequent EEG reading;

confirming that the subsequent EEG reading corresponds to the user specific EEG profile for the user by using a comparative spectral analysis of the subsequent EEG reading and the baseline EEG reading and identifying that predetermined attributes of the subsequent EEG reading match the predetermined attributes of the baseline EEG reading associated with the user;

in response to confirming that the subsequent EEG reading corresponds to the user specific EEG profile, transmitting a third control signal to the user device, wherein the third control signal is configured to customize a component of the user device in accordance with the user preferences for experience modification, wherein customizing the component of the user device causes a change in the user's experience, and wherein the user's experience comprises experience of the one or more visual or auditory stimuli;

transmitting a fourth control signal to cause the EEG reader to capture a second subsequent EEG reading after the change in the user's experience;

receiving, from the EEG reader, the second subsequent EEG reading; and confirming that the second subsequent EEG reading corresponds to a predetermined user reaction for the user by using a second comparative spectral analysis of the second subsequent EEG reading.

16. The computer-implemented method of claim 15, wherein the third control signal transmitted to the user device is configured to customize the component of the user device in response to the subsequent EEG reading by applying a stored selected user preference associated with the user activity and the user device, wherein the stored selected user preference is one of the stored selected user preferences in the user data repository.

17. The computer-implemented method of claim 15, wherein the computer processing device further performs the following operations:

receiving, from the EEG reader, the subsequent EEG reading; and transmitting, to a third party system, a fifth control signal, wherein the fifth control signal is configured to customize a component of the third party system and wherein customizing the component of the third party system changes the user's experience at the third party system.

18. The computer-implemented method of claim 15, wherein performing the comparative spectral analysis of the subsequent EEG reading and the baseline EEG reading further includes comparing predetermined attributes of the baseline EEG reading and the subsequent EEG reading to identify a match or partial match for the user; and generating a confidence that the subsequent EEG reading is an EEG reading of the user based on a comparative analysis to the baseline EEG reading for the user.

19. The computer-implemented method of claim 15, wherein generating the user specific EEG profile for the user further comprises:

analyzing frequency content for the baseline EEG reading time-locked to a known event or stimulus;

detecting periodicities, patterns, and component frequencies present in the baseline EEG reading; and storing the periodicities, patterns, and component frequencies for the baseline EEG reading in the user specific EEG profile.

20. The computer-implemented method of claim 15, wherein the system is further configured to interface with multiple users at one time; and transmit a series of control signals to customize discrete components of the user device, a set of user devices, or a smart system in response to subsequent EEG readings for the multiple users, wherein customizing the discrete components causes a change in the experience of each of the multiple users.

* * * * *